United States Patent
Hixon et al.

(10) Patent No.: US 8,911,433 B2
(45) Date of Patent: Dec. 16, 2014

(54) METHODS AND APPARATUS RELATED TO A DISTAL END OF A SIDE-FIRE OPTICAL FIBER HAVING MULTIPLE CAPILLARY COMPONENTS

(75) Inventors: Jessica Hixon, Watertown, MA (US); Christopher Oskin, Grafton, MA (US); Richard Tumminelli, Ashland, MA (US)

(73) Assignees: Boston Scientific Scimed, Inc., Maple Grove, MN (US); Coherent, Inc., Santa Clara, CA (US)

( * ) Notice: Subject to any disclaimer, the term of this patent is extended or adjusted under 35 U.S.C. 154(b) by 658 days.

(21) Appl. No.: 12/947,365

(22) Filed: Nov. 16, 2010

(65) Prior Publication Data
US 2011/0176772 A1    Jul. 21, 2011

Related U.S. Application Data (60) Provisional application No. 61/262,404, filed on Nov. 18, 2009.

(51) Int. Cl.
| | | |
|---|---|---|
| A61B 18/22 | (2006.01) | |
| A61B 18/20 | (2006.01) | |
| A61B 18/18 | (2006.01) | |
| G02B 6/02 | (2006.01) | |
| G02B 6/036 | (2006.01) | |
| G02B 6/36 | (2006.01) | |
| F21V 8/00 | (2006.01) | |
| G02B 6/26 | (2006.01) | |
| A61B 18/00 | (2006.01) | |
| A61B 17/00 | (2006.01) | |

(52) U.S. Cl.
CPC .............. *G02B 6/3624* (2013.01); *A61B 18/20* (2013.01); *A61B 18/22* (2013.01); *G02B 6/001* (2013.01); *G02B 6/262* (2013.01); *A61B 2018/00547* (2013.01); *A61B 2017/00274* (2013.01); *A61B 2018/2272* (2013.01)
USPC ............... 606/16; 606/15; 385/123; 385/124; 385/126; 385/127

(58) Field of Classification Search
None
See application file for complete search history.

(56) References Cited

U.S. PATENT DOCUMENTS

| | | | | |
|---|---|---|---|---|
| 4,662,368 A | * | 5/1987 | Hussein et al. | .................. 606/15 |
| 4,740,047 A | | 4/1988 | Abe et al. | |

(Continued)

OTHER PUBLICATIONS

Invitation to Pay Additional Fees and, Where Applicable, Protest Fee, and Partial International Search Report issued in corresponding application PCT/US2010/056827, mailed on Feb. 4, 2011, 6 pages.

(Continued)

*Primary Examiner* — Lynsey Crandall
*Assistant Examiner* — Manolis Pahakis
(74) *Attorney, Agent, or Firm* — Bookoff McAndrews, PLLC (57) ABSTRACT

In one embodiment, an apparatus may include a first capillary component. A second capillary component may be disposed outside of the first capillary component and may have an inner surface, wherein a portion of the inner surface may be heat-fused to an outer surface of the first capillary component. The apparatus may also include a portion of an optical fiber disposed inside of the first capillary component and the portion of the optical fiber can have an outer surface. A portion of the outer surface of the optical fiber may be heat-fused to an inner surface of the first capillary component. The optical fiber may have a distal surface configured to reflect electromagnetic radiation propagated along a longitudinal axis of a distal end portion of the optical fiber in a lateral direction through the inner surface of the first capillary component and the inner surface of the second capillary component.

20 Claims, 6 Drawing Sheets

(56) References Cited

U.S. PATENT DOCUMENTS

| | | | | |
|---|---|---|---|---|
| 5,074,632 | A | * | 12/1991 | Potter ............................. 385/31 |
| 5,129,895 | A | * | 7/1992 | Vassiliadis et al. ............... 606/6 |
| 5,151,096 | A | * | 9/1992 | Khoury ........................... 606/15 |
| 5,196,005 | A | * | 3/1993 | Doiron et al. .................... 606/7 |
| 5,242,438 | A | * | 9/1993 | Saadatmanesh et al. ....... 606/15 |
| 5,253,312 | A | * | 10/1993 | Payne et al. ..................... 385/31 |
| 5,254,114 | A | * | 10/1993 | Reed et al. ...................... 606/15 |
| 5,269,777 | A | * | 12/1993 | Doiron et al. ................... 606/7 |
| 5,292,320 | A | * | 3/1994 | Brown et al. .................... 606/15 |
| 5,337,381 | A | * | 8/1994 | Biswas et al. ................... 385/36 |
| 5,409,483 | A | * | 4/1995 | Campbell et al. ................ 606/15 |
| 5,428,699 | A | * | 6/1995 | Pon ................................. 385/31 |
| 5,496,307 | A | * | 3/1996 | Daikuzono ...................... 606/15 |
| 5,509,917 | A | * | 4/1996 | Cecchetti et al. ............... 606/15 |
| 5,530,709 | A | | 6/1996 | Waarts et al. |
| 5,562,657 | A | | 10/1996 | Griffin |
| 5,571,099 | A | * | 11/1996 | Purcell et al. ................... 606/17 |
| 5,649,924 | A | * | 7/1997 | Everett et al. ................... 606/15 |
| 5,772,657 | A | | 6/1998 | Hmelar et al. |
| 5,908,415 | A | * | 6/1999 | Sinofsky .......................... 606/7 |
| 6,168,591 | B1 | | 1/2001 | Sinofsky .......................... 606/15 |
| 6,270,492 | B1 | * | 8/2001 | Sinofsky .......................... 606/15 |
| 6,282,349 | B1 | | 8/2001 | Griffin |
| 6,296,608 | B1 | | 10/2001 | Daniels et al. |
| 6,347,178 | B1 | | 2/2002 | Edwards et al. |
| 6,522,806 | B1 | * | 2/2003 | James et al. ..................... 385/31 |
| 6,522,827 | B1 | * | 2/2003 | Loeb et al. ...................... 385/147 |
| 6,562,028 | B2 | | 5/2003 | Nield et al. ...................... 606/15 |
| 6,564,087 | B1 | * | 5/2003 | Pitris et al. ...................... 600/478 |
| 6,615,072 | B1 | * | 9/2003 | Izatt et al. ....................... 600/478 |
| 6,687,436 | B2 | * | 2/2004 | Griffin ............................. 385/43 |
| 6,860,651 | B2 | * | 3/2005 | DeRosa et al. .................. 385/92 |
| 6,986,764 | B2 | | 1/2006 | Davenport et al. |
| 7,169,140 | B1 | | 1/2007 | Kume |
| 7,221,840 | B2 | | 5/2007 | Vienne et al. |
| 7,228,033 | B2 | | 6/2007 | Bhagavatula et al. |
| 7,274,843 | B2 | * | 9/2007 | James et al. ..................... 385/31 |
| 7,309,167 | B2 | | 12/2007 | Stephen |
| 7,412,141 | B2 | * | 8/2008 | Gowda et al. ................... 385/117 |
| 7,447,409 | B2 | | 11/2008 | Griffin |
| 7,492,987 | B2 | | 2/2009 | Yeik et al. |
| 8,073,297 | B2 | * | 12/2011 | Griffin ............................. 385/33 |
| 8,285,097 | B2 | * | 10/2012 | Griffin ............................. 385/117 |
| 8,358,890 | B2 | * | 1/2013 | Zerfas et al. .................... 385/39 |
| 8,731,351 | B2 | * | 5/2014 | Fairneny et al. ................ 385/38 |
| 2003/0135205 | A1 | * | 7/2003 | Davenport et al. ............. 606/3 |
| 2005/0203419 | A1 | * | 9/2005 | Ramanujam et al. .......... 600/473 |
| 2006/0078265 | A1 | * | 4/2006 | Loeb ............................... 385/141 |
| 2006/0084959 | A1 | * | 4/2006 | Davenport et al. ............. 606/15 |
| 2006/0285793 | A1 | * | 12/2006 | Brekke et al. ................... 385/31 |
| 2007/0106286 | A1 | * | 5/2007 | Harschack et al. ............. 606/17 |
| 2007/0179485 | A1 | * | 8/2007 | Yeik et al. ....................... 606/15 |
| 2008/0147150 | A1 | * | 6/2008 | Xiong et al. .................... 607/93 |
| 2008/0247714 | A1 | * | 10/2008 | Nakamura et al. .............. 385/96 |
| 2009/0287198 | A1 | * | 11/2009 | Hanley et al. ................... 606/15 |
| 2009/0287199 | A1 | * | 11/2009 | Hanley et al. ................... 606/15 |
| 2009/0287200 | A1 | * | 11/2009 | Hanley et al. ................... 606/15 |
| 2009/0299352 | A1 | * | 12/2009 | Zerfas et al. .................... 606/15 |
| 2009/0326525 | A1 | * | 12/2009 | Hixon et al. .................... 606/15 |
| 2010/0016845 | A1 | * | 1/2010 | Hanley et al. ................... 606/15 |
| 2010/0198009 | A1 | | 8/2010 | Farr et al. |
| 2011/0255828 | A1 | * | 10/2011 | Sudarshanam ................. 385/31 |

OTHER PUBLICATIONS

Encyclopedia of Laser Physics, RP Photonics Consulting GmBH, Dr. Rüdiger Paschotta, "Dielectric Coatings," Aug. 19, 2008, 5 pages.
Notification of Transmittal of the International Search Report and the Written Opinion of the International Searching Authority issued in corresponding international application No. PCT/US2010/056827, mailed on May 19, 2011, 17 pages.

* cited by examiner

METHODS AND APPARATUS RELATED TO A DISTAL END OF A SIDE-FIRE OPTICAL FIBER HAVING MULTIPLE CAPILLARY COMPONENTS

CROSS REFERENCE TO RELATED APPLICATION

This Nonprovisional Patent Application claims the benefit of priority under 35 U.S.C. §119 to U.S. Provisional Patent Application No. 61/262,404, filed Nov. 18, 2009, and titled "METHODS AND APPARATUS RELATED TO A DISTAL END OF A SIDE-FIRE OPTICAL FIBER HAVING MULTIPLE CAPILLARY COMPONENTS," which is incorporated herein by reference.

FIELD OF THE INVENTION

Embodiments relate generally to optical medical devices, and, in particular, to side-fire optical fibers and methods for using such devices.

BACKGROUND OF THE INVENTION

During some laser-based surgical procedures, a side-fire optical fiber can provide a medical practitioner with more control than a straight-firing optical fiber system when applying laser energy to a treatment area. For example, laser energy can be emitted precisely towards a target area in a lateral direction via an angled surface of an optical fiber of the side-fire optical fiber. Even if carefully manufactured using known manufacturing techniques, a side-fire optical fiber can be susceptible to, for example, undesirable laser energy leakage and/or premature failure.

Thus, a need exists for methods and apparatus related to a side-fire optical fiber that can increase device longevity, increase laser energy transmission efficiency, reduce overheating, and/or increase patient safety.

SUMMARY OF THE INVENTION

An aspect of the present disclosure may include an apparatus having a first capillary component and a second capillary component. The second capillary component may be disposed outside of the first capillary component and may include an inner surface, wherein at least a portion of the inner surface may be heat-fused to an outer surface of the first capillary component. The apparatus may further include a portion of an optical fiber disposed inside of the first capillary component. The portion of the optical fiber may include an outer surface wherein a portion of the outer surface of the optical fiber may be heat-fused to an inner surface of the first capillary component and the optical fiber may have a distal surface configured to reflect electromagnetic radiation propagated along a longitudinal axis of a distal end portion of the optical fiber in a lateral direction through the inner surface of the first capillary component and the inner surface of the second capillary component.

Various embodiments of the disclosure may include one or more of the following aspects: an outer cover coupled to and disposed outside of the second capillary component, the outer cover may have an opening configured such that the electromagnetic radiation is emitted through the opening when laterally reflected from the distal surface; the distal surface of the portion of the optical fiber and a distal surface of the first capillary component may collectively define a substantially flat surface non-normal to the longitudinal axis; the portion of the optical fiber may be a first portion of the optical fiber, and the optical fiber may further include a second portion, wherein the second capillary component has a proximal end disposed outside of a portion of a polymer-based jacket around a cladding layer of the second portion of the optical fiber, wherein the second portion of the optical fiber may be mutually exclusive from the first portion of the optical fiber; the portion of the optical fiber may be a first portion of the optical fiber, and the optical fiber may further include a second portion mutually exclusive from and abutting the first portion of the optical fiber, wherein the apparatus may further include an outer cover coupled to and disposed outside of the second capillary component, and the outer cover may have a proximal portion in contact with a polymer-based jacket around a cladding layer of the second portion of the optical fiber; the optical fiber may have a dopant different than a dopant of the first capillary component, and the portion of the optical fiber may include at least one cladding layer; and the distal surface of the optical fiber and a distal end portion of the second capillary component may define at least a portion of an enclosure.

An aspect of the present disclosure may include a method including polishing a first capillary component heat-fused to an optical fiber. The polishing may be performed such that a portion of the first capillary component and a portion of the optical fiber may define a distal surface disposed within a plane non-normal to a longitudinal axis of the portion of the optical fiber. The method may further include moving a second capillary component over the distal surface such that at least a portion of the first capillary component may be disposed between at least a portion of an inner surface of the second capillary component and the portion of the optical fiber. Further, the method may include heating at least a portion of the inner surface of the second capillary component so that the portion of the inner surface of the second capillary component may be heat-fused to the outer surface of the portion of the first capillary component.

Various embodiments of the disclosure may include one or more of the following aspects: cutting the first capillary component from a silica-based pre-form, and moving an inner surface of the portion of the first capillary component over an outer surface of the optical fiber before the polishing; heating an inner surface of the portion of the first capillary component and an outer surface of the optical fiber such that the inner surface of the portion of the first capillary component may be heat-fused to at least a portion of the outer surface of the optical fiber; the optical fiber may be a silica-based optical fiber that may have a cladding layer and the method may further include removing at least a portion of a polymer-based jacket disposed outside of the cladding layer which may expose a portion of the cladding layer, and moving an inner surface of the first capillary component over the exposed portion of the cladding layer before the polishing; and heating a distal end of the second capillary component such that an air pocket may be defined by the distal end of the second capillary component and the distal surface.

An aspect of the present disclosure may include an apparatus having a distal surface of a side-fire laser fiber defined by a first silica-based capillary component and an optical fiber. The first silica-based capillary component may be heat-fused to an outer surface of the optical fiber, and the distal surface may be within a plane non-normal to a longitudinal centerline of the optical fiber. The apparatus may further include a second silica-based capillary component which may be heat-fused to an outer surface of the first silica-based capillary component.

Various embodiments of the disclosure may include one or more of the following aspects: the first silica-based capillary component may have a length less than a length of the second silica-based capillary component; at least one of substantially an entirety of the outer surface of the first silica-based capillary component is heat-fused to the second silica-based capillary component, or substantially an entirety of the inner surface of the first silica-based capillary component is heat-fused to the outer surface of the optical fiber; the outer surface of the first silica-based capillary component may be heat-fused to the second silica-based capillary component at a first region and the outer surface of the first silica-based capillary component may be heat-fused to the second silica-based capillary component at a second region noncontiguous with the first region; an outer diameter of the first silica-based capillary component may be substantially equal to an outer diameter of a polymer-based jacket of the optical fiber around a cladding layer of the optical fiber; the first capillary component may have a dopant profile different than a dopant profile of the second capillary component; the second capillary component may have a tubular portion and a cap, wherein the first capillary component may define a lumen therethrough; and the first silica-based capillary component may have an index of refraction that is different than an index of refraction of the optical fiber, and the index of refraction of the first silica-based capillary component may be substantially equal to an index of refraction of the second silica-based capillary component.

Additional objects and advantages of the disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present embodiments (exemplary embodiments) of the invention, examples of which are illustrated in the accompanying drawings. Wherever possible, the same reference numbers will be used throughout the drawings to refer to the same or like parts.

The devices and methods described herein are generally related to a side-fire member configured to treat an area within a body of a patient. Specifically, the side-fire member can be used to transmit laser energy from a laser source to a target treatment area that is disposed lateral to a distal end portion (e.g., a side-fire assembly) of the side-fire member. One end of the side-fire member, the proximal end portion, can be coupled to the laser source while the other end of the side-fire member, the distal end portion, can be inserted into the patient's body to provide the laser treatment.

An optical fiber within the side-fire member can have a surface non-normal and non-parallel to a longitudinal axis (or centerline) of a distal end portion of the optical fiber. The surface can be referred to as an angled surface and can be at the distal end of the optical fiber. The angled surface can define a portion of an interface (can be referred to as a reflective interface) configured to redirect laser energy propagated from within the optical fiber and incident on the interface to a direction offset (e.g., a lateral direction, a side-firing direction) from the longitudinal axis toward the target treatment area. The laser energy redirected via the interface can be referred to as lateral laser energy, redirected laser energy, or side-fired laser energy. Because the optical fiber is configured to redirect laser energy in, for example, a lateral direction, the optical fiber can be referred to as a side-fire optical fiber. The optical fiber and/or laser source can be included in a side-fire system (also can be referred to as an optical fiber system).

The angled surface of the optical fiber can be disposed within multiple capillary components (e.g., doped silica ($SiO_2$) capillary components, silica-based capillary components) that are coupled to (e.g., fused to, heat-fused to) one another and/or the optical fiber. At least a portion of the capillary components and a distal end portion of the optical fiber can collectively define at least a portion of an angled surface. Laser energy redirected by the angled surface can be transmitted through one or more of the capillary components. In some embodiments, an outer cover (e.g., a metallic cap, a polymer-based cap) can be disposed outside of the capillary components and the optical fiber. The outer cover can be substantially opaque to a spectral region of electromagnetic radiation associated with the laser energy propagated within the optical fiber. In some embodiments, the outer cover can have a transmissive portion (e.g., a window or an opening) through which redirected laser energy can be transmitted. In some embodiments, one or more of the capillary components and the angled surface of the optical component can define an enclosure. The optical fiber, the capillary components, and the outer cover can collectively define and can be referred to as a side-fire assembly of an optical fiber system or as a laterally-firing end of an optical fiber system.

In some embodiments, at least a portion of the side-fire assembly can be produced by disposing multiple coupled capillary components around an angled surface configured to redirect laser energy in a lateral direction. For example, at least a portion of the side-fire assembly can include a first capillary component disposed outside of and heat-fused during a first heat-fusing process to a distal portion of an optical fiber. Then, the first capillary component and the distal end portion of the optical fiber can be cleaved (and polished) to define an angled surface. Then a second capillary component disposed outside of the first capillary component can be heat-fused to the first capillary component during a second heat-fusing process. The angled surface can be defined after the first capillary component has been heat-fused to the optical fiber, so that a portion of the angled surface defined by the optical fiber can be defined as a substantially flat surface without, for example, being deformed (e.g., warped) during the first heat-fusing process. The first capillary component can function as a thermal insulator that protects the angled surface defined by the optical fiber during the second heat-fusing process. If instead the first capillary component was heat-fused to the distal end portion of the optical fiber after the distal end portion of the optical fiber has been cleaved (and polished), the heat-fusing could result in damage to the angled surface.

In some embodiments, an index of refraction of the capillary components can be defined to promote total or substantially total internal reflection of, for example, leaked/stray laser energy from within the optical fiber and incident on interfaces defined by the capillary components and/or the optical fiber. By internally reflecting the leaked/stray laser energy, the leaked/stray energy can be substantially prevented from, for example, adversely affecting the mechanical and/or optical properties of the optical fiber. In some embodiments, the index of refraction of the capillary components can be defined at least in part by a doping concentration of a dopant (e.g., a fluorine dopant, a chlorine dopant, a rare-earth dopant, a germanium dopant, an alkali metal dopant, an alkali metal oxide dopant, etc.) within the capillary components. The optical fiber can be optionally doped with any dopant that can be used to dope the capillary components, and vice versa.

The devices and methods described herein can be used in treating symptoms related to, for example, an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer layer of tissue and is located below the bladder and surrounding the urethra, the canal through which urine passes out of the body. Prostate growth can occur in different types of tissue and can affect men differently. As a result of these differences, treatment varies in each case. No cure for BPH exists, and once the prostate begins to enlarge, it often continues, unless medical treatment is initiated.

Patients who develop symptoms associated with BPH generally require some form of treatment. When the prostate gland is mildly enlarged, research studies indicate that early treatment may not be needed because the symptoms can clear up without treatment in as many as one-third of cases. Instead of immediate treatment, regular checkups are recommended. Only if the condition presents a health risk, or the symptoms result in major discomfort or inconvenience to the patient, is treatment generally recommended. Current forms of treatment include drug treatment, minimally-invasive therapy, and surgical treatment. Drug treatment is not effective in all cases and a number of medical procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-fire optical fibers and high-power laser sources have been used to remove obstructing prostate tissue. In these procedures, a doctor passes the optical fiber through the urethra using a cystoscope, a specialized endoscope with a small camera on the end, and then delivers multiple bursts of laser energy to destroy some of the enlarged prostate tissue and to shrink the size of the prostate. Patients who undergo laser surgery usually do not require overnight hospitalization, and in most cases, the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nanometers (nm). This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cubic centimeters (cc). Laser-based surgical procedures, such as HoLAP and HoLEP, are often preferred because they produce similar results to those obtained from TURP surgery while having fewer complications and requiring shorter hospital stay, shorter catheterization time, and shorter recovery time.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a medical practitioner, a nurse, a technician, etc.) who would insert the medical device into the patient. Thus, for example, the optical fiber end inserted inside a patient's body would be the distal end of the optical fiber, while the optical fiber end outside a patient's body would be the proximal end of the optical fiber.

Figure 1:
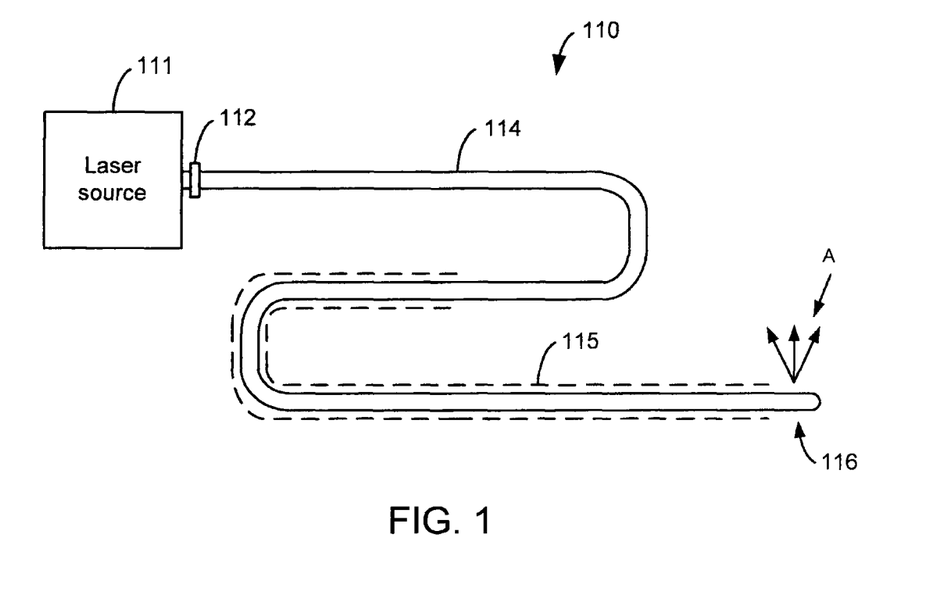
FIG. 1 is a schematic diagram of a side-fire system, according to an embodiment.

FIG. 1 is a schematic diagram of a side-fire system 110, according to an embodiment. The side-fire system 110 can include a laser source 111, an optical coupler 112, a side-fire member 114, and a side-fire assembly 116. The side-fire system 110 also includes a suitable catheter or endoscope 115 for inserting the side-fire assembly 116 into a patient's body.

The laser source 111 can be configured to generate laser energy that can be propagated within the side-fire member 114, for example, during a surgical procedure. The laser source 111 can include, for example, a Ho:YAG laser source, a neodymium-doped:YAG (Nd:YAG) laser source, a semiconductor laser diode, and/or a laser source employing a non-linear element (e.g., a laser source that includes a potassium-titanyl phosphate crystal (KTP) laser source). In some embodiments, more than one laser source can be used during a surgical procedure.

In some embodiments, the laser source 111 can also have a control module (not shown) configured to control (e.g., to set, to modify) a timing, a wavelength, and/or a power of laser energy emitted from the laser source 111. In some embodiments, the control module can also be configured to perform various functions such as laser selection, filtering, temperature compensation, and/or Q-switching. The control module can be a hardware-based control module and/or a software-based control module that can include, for example, a processor and/or a memory.

The side-fire member 114 can be coupled to the laser source 111 through the optical coupler 112. The optical coupler 112 can be, for example, a Sub-Miniature A (SMA) connector. The proximal end of the side-fire member 114 can be configured to receive laser energy from the laser source 111, and the distal end of the side-fire member 114 can be configured to output the laser energy 120 through the side-fire assembly 116. The side-fire member 114 can include an optical fiber that has, for example, a fiber core, one or more cladding layers disposed around the fiber core, a buffer layer disposed around the cladding layer(s), and a jacket (disposed around the buffer layer). In some embodiments, the buffer layer can be referred to as a cladding layer.

In some embodiments, the fiber core can be made of a suitable material for the transmission of laser energy from the laser source 111. In some embodiments, for example, the fiber core can be made of silica with a low hydroxyl ($OH^-$) ion residual concentration. Laser energy wavelengths ranging from about 500 nm to about 2100 nm can be propagated within the fiber core during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a dopant (e.g., an amplifying dopant). The cladding can be a single or a double cladding that can be made of a hard polymer or silica. The buffer (which can function as a cladding layer) can be made of a hard polymer or acrylate, for example. When the optical fiber includes a jacket, the jacket can be made of Tefzel®, for example, or can be made of other polymer-based substances.

The side-fire assembly 116 can include one or more surfaces that can individually or collectively operate to redirect laser energy in a direction non-parallel (e.g., a lateral direction) to a longitudinal axis or a centerline of the distal end of the fiber core. Such an surface can be an angled surface defined by, for example, the fiber core, one or more cladding layers about the fiber core, and/or a buffer layer. The angled surface can be non-normal to a longitudinal axis (or centerline) of a distal end portion of the optical fiber. In some embodiments, the angled surface can be, for example, a reflecting member with a multilayer dielectric coating on an angled surface. More details related to an example of a reflecting member are set forth in co-pending patent application Ser. No. 61/054,280, entitled, "Side-Firing Laser Fiber with Protective Tip and Related Methods," filed May 19, 2008, which is incorporated herein by reference in its entirety.

The surface(s) configured to redirect laser energy can be disposed within multiple capillary components at the side-fire assembly 116 of the side-fire member 114. The capillary components can be disposed outside of an optical fiber of the side-fire member 114. For example, a first capillary component can be heat-fused to a cladding layer of the optical fiber of the side-fire member 114. The first capillary component can define at least a portion of an enclosure. A second capillary component can be disposed outside of the first capillary component and heat-fused to the first capillary component. In some embodiments, an outer cover, such as a metal cap, can be coupled to an outer surface of the second capillary component. Because the second capillary component is disposed outside of the first capillary component, the second capillary component can be referred to as an outer capillary component and the first capillary component can be referred to as an inner capillary component.

In some embodiments, the endoscope 115 can define one or more lumens (also can be referred to as working channels). In some embodiments, the endoscope 115 can include a single lumen that can receive therethrough various components such as the side-fire member 114. The endoscope 115 can have a proximal end configured to receive the side-fire assembly 116 of the side-fire member 114 and a distal end configured to be inserted into a patient's body for positioning the side-fire assembly 116 of the side-fire member 114 in an appropriate location for a laser-based surgical procedure. For example, to relieve symptoms associated with BPH, the endoscope 115 can be used to place the optical-fiber side-fire assembly 116 at or near the enlarged portion of the prostate gland. The endoscope 115 can include an elongate portion that can be sufficiently flexible (or rigid) to allow the elongate portion to be maneuvered within the body.

The endoscope 115 can also be configured to receive various medical devices or tools through one or more lumens of the endoscope, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope 115 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 115, for example, and coupled to a proximal end portion of an optical fiber that can be disposed within a lumen of the endoscope 115. Such an embodiment allows a medical practitioner to view the interior of a patient's body through the eyepiece.

Figure 2:
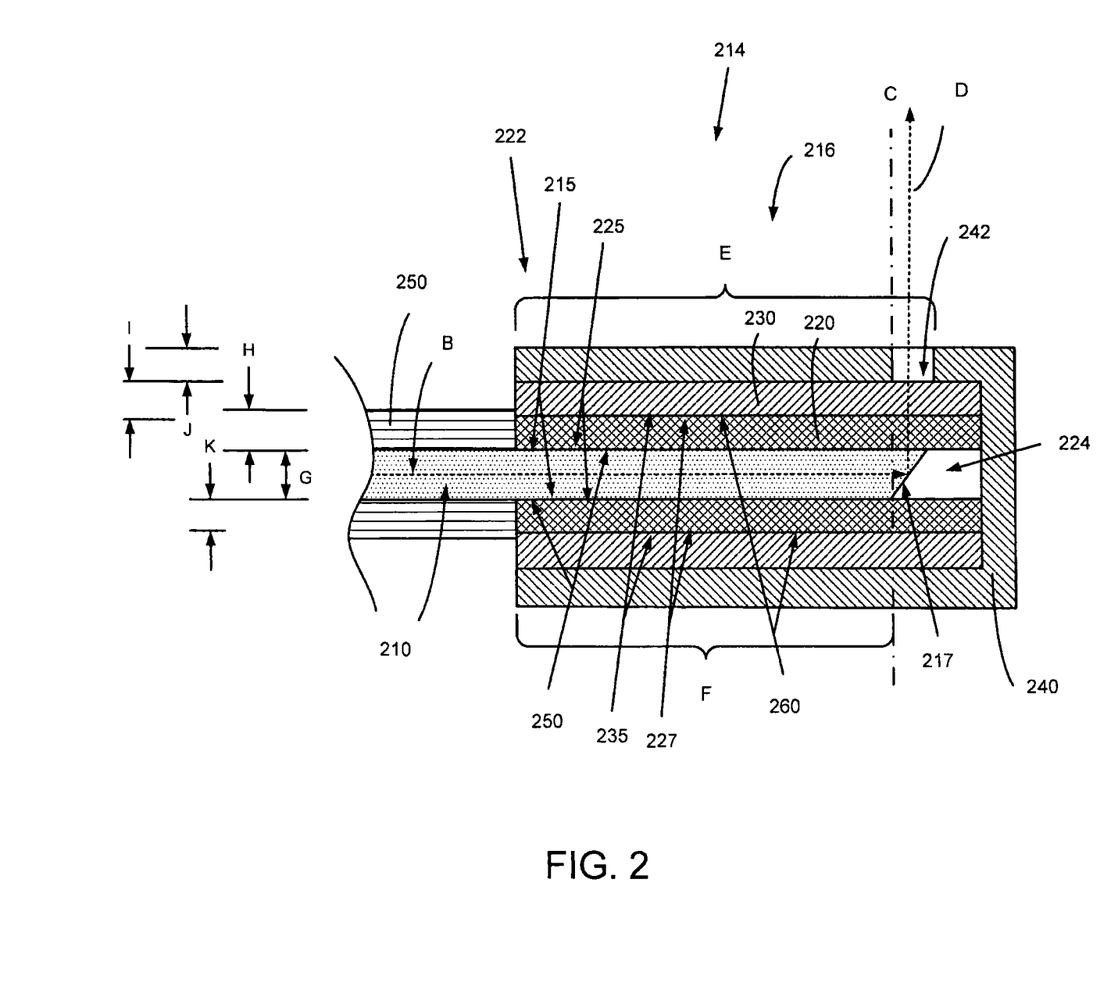
FIG. 2 is a side cross-sectional view of a side-fire assembly of a side-fire member that has two capillary components, according to an embodiment.

FIG. 2 is a side cross-sectional view of a side-fire assembly 216 of a side-fire member 214 that has two capillary components, according to an embodiment. The capillary components include a first capillary component 220 and a second capillary component 230. The first capillary component 220 is disposed outside of an optical fiber 210 of the side-fire member 214 and inside of the second capillary component 230. An outer cover 240 (e.g., a metal cover) is coupled to and disposed outside of the second capillary component 230. The optical fiber 210, the first capillary component 220, and/or the second capillary component 230 can be made from a silica-based material (e.g., a pure (or substantially pure) silica material (without a dopant), a doped silica material).

As shown in FIG. 2, laser energy B is propagated along a longitudinal axis (or centerline) of the optical fiber 210 of the side-fire member 214 and is redirected by an interface defined by an angled surface 217 and a gas (or a liquid) within a cavity 224. The cavity 224 is defined by the first capillary component 220, the angled surface 217, and the outer cover 240. In some embodiments, the gas can be air. The redirected laser energy D is transmitted through a portion of the first capillary component 220, a portion of the second capillary component 230, and an opening 242 defined by the outer cover 240. In other words, the laser energy B is transmitted within an optical path along the longitudinal axis (or centerline) of the optical fiber 210, and the redirected laser energy D is transmitted within an optical path that intersects the first capillary component 220, the second capillary component 230, and the opening 242. In some embodiments, the optical path(s) can include multiple segments. Although not shown, the optical fiber 210 can have, for example, a fiber core, one or more cladding layers around the fiber core, and/or a buffer layer (which can function as a cladding layer or the only cladding layer). As shown in FIG. 2, a jacket layer 250 is disposed around a portion of the optical fiber 210.

The first capillary component 220 has an inner surface 225 that is heat-fused to an outer surface 215 of the optical fiber 210. Specifically, the inner surface 225 is heat-fused over substantially an entire area of the outer surface 215 of the optical fiber 210 that is disposed within the first capillary component 220 (except for the angled surface 217, which is not part of the outer surface 215). In other words, any portion of the outer surface 215 of the optical fiber 210 that is substantially parallel to, and disposed within the first capillary component 220, is heat-fused to the inner surface 225 of the first capillary component 220. Because the optical fiber 210 has an angled surface 217, a heat-fused length E along a top side of the optical fiber 210 is longer than a heat-fused length F along a bottom side of the optical fiber 210. As shown in FIG. 2, an interface 250 can be defined by the inner surface 225 of the first capillary component 220 and the outer surface 215 of the optical fiber 210.

The second capillary component 230 has an inner surface 235 that is heat-fused to an outer surface 227 of the first capillary component 220. Specifically, the inner surface 235 of the second capillary component 230 is heat-fused over substantially an entire area of the outer surface 227 of the first capillary component 220 that is disposed within the second capillary component 230. In other words, any portion of the outer surface 227 of the first capillary component 220 that is substantially parallel to, and disposed within the second capillary component 230, is heat-fused to the inner surface 235 of the second capillary component 230. As shown in FIG. 2, an interface 260 can be defined by the inner surface 235 of the second capillary component 230 and the outer surface 227 of the first capillary component 220.

In some embodiments, less than the entire area of the outer surface 215 of the optical fiber 210 can be heat-fused to the inner surface 225 of the first capillary component 220. Similarly, in some embodiments, less than the entire area of the outer surface 227 of the first capillary component 220 can be heat-fused to the inner surface 235 of the second capillary component 230. For example, in some embodiments, a portion of the outer surface 215 of the optical fiber 210 that is proximal to a plane C, which is at a proximal end of the angled surface 217 and substantially normal to a longitudinal axis (or centerline) of the optical fiber 210, can be heat-fused to the first capillary component 220, and the portion of the outer surface 215 of the optical fiber 210 that is distal to the place C is not heat-fused.

In some embodiments, multiple locations (e.g., at multiple random locations, at multiple locations in a pattern) along the outer surface 215 of the optical fiber 210 can be heat-fused to the inner surface 225 of the first capillary component 220, and/or multiple locations along the outer surface 227 of the first capillary component 220 can be heat-fused to the inner surface 235 of the second capillary component 230. For example, a portion of the outer surface 215 of the optical fiber 210 near a proximal end 222 of the side-fire assembly 216 and/or a portion of the outer surface 215 of the optical fiber 210 near the angled surface 217 can be heat-fused to the inner surface 225 of the first capillary component 220. In some embodiments, for example, two or more circumferential portions (or non-circumferential portions) of the outer surface 215 can be heat-fused to the first capillary component 220.

In some embodiments, the heat-fused portions do not continuously surround the optical fiber 210 and/or the first capillary component 220. In other words, just a portion of the circumference (e.g., a top portion and/or a bottom portion) of the outer surface 215 of the optical fiber 210 can be heat-fused to the first capillary component 220, and/or just a portion of the circumference (e.g., a top portion and/or a bottom portion) of the outer surface 227 of the first capillary component 220 can be heat-fused to the second capillary component 230. In some embodiments, the portions that are heat-fused can be aligned with an area through which the laser will be directed (to prevent unwanted reflection from an unfused interfaces). The heat-fused area between the optical fiber 210 and the first capillary component 220 can be sufficiently large to provide mechanical stability (e.g., resistance to shear forces) between the optical fiber 210 and the first capillary component 220, and/or the heat-fused area between the first capillary component 220 and the second capillary component 230 can be sufficiently large to provide mechanical stability (e.g., resistance to shear forces) between the first capillary component 220 and the second capillary component 230.

In some embodiments, the first capillary component 220, the second capillary component 230, and/or the optical fiber 210 can be made of various materials. For example, the first capillary component 220 and the second capillary component 230 can be made from substantially the same doped silica material (e.g., a fluorine-doped silica material), and the optical fiber 210 can be made from a substantially different doped silica material (e.g., a substantially pure optical fiber core surrounded by a lightly doped fluorinated cladding). In some embodiments, for example, the second capillary component 230 can be made of an undoped silica material and the first capillary component 220 can be made of a doped silica material, and vice versa.

In some embodiments, the first capillary component 220 can be made of a material that has an index of refraction that is different than an index of refraction of a material of the optical fiber 210 and/or an index of refraction of a material of the second capillary component 230. For example, the inner surface 225 of the first capillary component 220 can have an index of refraction less than an index of refraction of the outer surface 215 of the optical fiber 210, and vice versa. In some embodiments, a portion of the laser energy B propagated within the optical fiber 210 and incident on the interface 250 can be totally or substantially totally internally reflected within the optical fiber 210 because of an index of refraction on a side of the interface 250 that includes the first capillary component 220 can be lower than an index of refraction of a side of the interface 250 that includes the optical fiber 210. In some embodiments, a portion of the laser energy B propagated within the optical fiber 210 and incident on the interface 250 can be transmitted (e.g., partially transmitted, totally transmitted) into the first capillary component 220 because an index of refraction on the first capillary component 220 side of the interface can be higher than an index of refraction of the optical fiber 210 side of the interface 250. If the optical fiber 210 has a cladding layer (not shown), a portion of the laser energy B propagated within the cladding layer and incident on the interface 250 can be totally (or substantially totally) internally reflected within the cladding layer.

In some embodiments, the second capillary component 230 can be made of a material that has an index of refraction that is different than an index of refraction of a material of the optical fiber 210 and/or an index of refraction of a material of the first capillary component 220. For example, the second capillary component 230 can be made of a material that has an index of refraction between an index of refraction of a material of the optical fiber 210 and an index of refraction of a material of the first capillary component 220. In some embodiments, for example, an index of refraction on a side of the interface 260 that includes the first capillary component 220 can be lower than an index of refraction of a side of the interface 260 that includes the second capillary component 230, or vice versa. In some embodiments, a portion of laser energy (not shown) propagated within the first capillary component 220 and incident on the interface 260 can be internally reflected (into the first capillary component 220) or transmitted (into the second capillary component 230) based on the relative indices of retraction of the first capillary component 220 and the second capillary component 230.

The index of refraction of the optical fiber 210, the first capillary component 220, and/or the second capillary component 230 can be defined by, for example, a concentration of a dopant (e.g., fluorine). For example, an index of refraction of the second capillary component 230 can be defined by a concentration of a fluorine dopant included in silica material used to make the second capillary component 230. In some embodiments, the doping concentration of the optical fiber 210, the first capillary component 220, and/or the second capillary component 230 can be substantially uniform. In some embodiments, the doping concentration of the optical fiber 210, the first capillary component 220, and/or the second capillary component 230 can be non-uniform (e.g., can have a gradient). For example, the doping concentration at the inner surface 225 of the first capillary component 220 can be lower than, for example, an outer surface 227 of the first capillary component 220, or vice versa.

The outer cover 240 can be configured to keep stray laser energy (e.g., a portion of stray laser energy from laser energy B) from being transmitted in an undesirable direction out of the side-fire assembly 216 of the side-fire member 214. Accordingly, the outer cover 240 can be substantially opaque to the laser energy B and/or configured to reflect and/or absorb stray laser energy within (e.g., internal to) the side-fire assembly 216 of the side-fire member 214. The outer cover 240 can also provide protection (e.g., mechanical protection) to the side-fire assembly 216 of the side-fire member 214. The outer cover 240 can be, for example, adhesively coupled to (e.g., adhesively coupled to using an epoxy), mechanically coupled to (e.g., mechanically coupled via a set screw and/or a press fit) the second capillary component 230.

In some embodiments, the outer cover 240 can be made of a metallic material such as a surgical grade (e.g., medical grade) stainless steel, a plastic, or other material with like properties. In some instances, the outer cover 240 can be made of a ceramic material (e.g., alumina) because certain ceramics can have stable material characteristics at high-temperatures and/or have a high reflectance value at desirable operating wavelengths of the laser energy B.

In some embodiments, rather than an opening 242, the outer cover 240 can include a transmissive material (not shown) through which the redirected laser energy D can be transmitted for surgical treatment. The transmissive material can be, for example, substantially transparent to a specified spectrum of electromagnetic radiation associated with the redirected laser energy D. The transmissive material can define, for example, a lens. In some embodiments, the transmissive material can be treated thermally, optically, mechanically, and/or chemically to define a desirable structural and/or optical characteristic. For example, the optically-transmissive material can be thermally treated during manufacturing using emissions from, for example, a carbon dioxide ($CO_2$) laser source. The transmissive material can be defined such that the redirected laser energy D can be delivered to a target area in a desirable fashion (e.g., delivered in a focused beam).

As shown in FIG. 2, the optical fiber 210 of the side-fire member 214 has an outer diameter G, for example, that can be between approximately a few micrometers ($\mu m$) (e.g., 20 $\mu m$) and hundreds of micrometers (e.g., 1500 $\mu m$). The jacket layer 250 around the optical fiber 210 can have a thickness H, for example, between a few micrometers (e.g., 5 $\mu m$) and hundreds of micrometers (e.g., 1500 $\mu m$). The first capillary component 220 can have a thickness K of between, for example, approximately a few micrometers (e.g., 5 $\mu m$) and several millimeters (mm) (e.g., 2 mm). As shown in FIG. 2, the thickness K of the first capillary component 220 is less than the thickness H of the jacket layer 250. The second capillary component 230 can have a thickness I of between, for example, approximately a few micrometers (e.g., 5 $\mu m$) and several millimeters (mm) (e.g., 2 mm). The outer cover 240 can have a thickness J of a few micrometers (e.g., 5 $\mu m$) and several millimeters (mm) (e.g., 2 mm). Although not shown, in some embodiments, the outer cover 240 can include a low-profile cover (e.g., a coating or a sleeve). In some embodiments, the thickness I and the thickness J can be substantially equal.

Although not shown, in some embodiments, the optical fiber 210 can have a fiber core with an outer diameter, for example, between a few micrometers ($\mu m$) (e.g., 20 $\mu m$) and hundreds of micrometers (e.g., 1200 $\mu m$). The optical fiber 210 can have a cladding layer that is approximately 1 to 1.3 times greater than the outer diameter of the fiber core. In some embodiments, the optical fiber 210 can have a cladding layer with a thickness between, for example, approximately a few micrometers (um) (e.g., 20 $\mu m$) and hundreds of micrometers (e.g., 1200 $\mu m$). The optical fiber 210 can also have a buffer layer with a thickness between, for example, approximately a few micrometers (um) (e.g., 20 $\mu m$) and hundreds of micrometers (e.g., 1200 $\mu m$).

In the embodiment shown in FIG. 2, the first capillary component 220 and the second capillary component 230 have a substantially equal length. In some embodiments, the first capillary component 220 can have a length that is different (e.g., shorter, longer) than a length of the second capillary component 230.

As shown in FIG. 2, the outer cover 240 has a proximal end, the proximal surface of which that is substantially within a plane that also includes a proximal end of the first capillary component 220 and a proximal end of the second capillary component 230. In some embodiments, the outer cover 240 can have a proximal end that is not aligned with a proximal end of the first capillary component 220 and/or a proximal end of the second capillary component 230.

Although not shown, in some embodiments, the side-fire assembly 214 can have more than two capillary components. In some embodiments, one or more of the capillary components may have one or more surfaces (e.g., an inner surface, an outer surface) that are not heat-fused. For example, in some embodiments, at least a portion of a side-fire assembly can be produced by heat-fusing a first capillary component disposed outside of a distal portion of an optical fiber to the optical fiber. The first capillary component and the distal end portion of the optical fiber can be cleaved (and polished) to define an angled surface. A second capillary component disposed outside of the first capillary component can be adhesively coupled to the first capillary component.

In some embodiments, the first capillary component 220 and/or the second capillary component 230 can define an enclosure (not shown). For example, the capillary component 220 and the angled surface 217 can define an enclosure (not shown). Specifically, a distal end portion of the first capillary component 220 can define a cap around the angled surface 217. In some embodiments, for example, the second capillary component 230 can define a cap (not shown) disposed outside of the first capillary component 220 shown in FIG. 2 (in such instances an enclosure would be defined by the cap of the second capillary component 220, the first capillary component 220, and the angled surface 217). In some embodiments, for example, a distal end portion of the second capillary component 230 can define a cap (not shown) disposed outside of the an enclosure defined by a cap at a distal end of the first capillary component 220 and the angled surface 217. In some embodiments, a cap and/or enclosure (not shown) defined by a distal end portion of the second capillary component 230 can be disposed within the outer cover 240.

In some embodiments, a distal end of the first capillary component 220 and/or second capillary component 230 can be heated while being pulled in distal direction (away from the angled surface 217) until an enclosure (and/or cap) is formed. For example, a force in the distal direction (away from the angled surface 217) can be applied on the distal end of the first capillary component 220 while it is being heated. The first capillary component 220 can be heated until the first capillary component 220 softens and can be pulled. As the distal end of the first capillary component 220 is heated and pulled, the first capillary component 220 can plastically deform until at least a portion of the distal end of the first capillary component 220 is separated from a proximal portion of the first capillary component 220 and the distal end of the first capillary component 220 defines a cap. More details related to a cap and/or enclosures are described in connection with at least FIGS. 3, 5F, and 5G.

Figure 3:
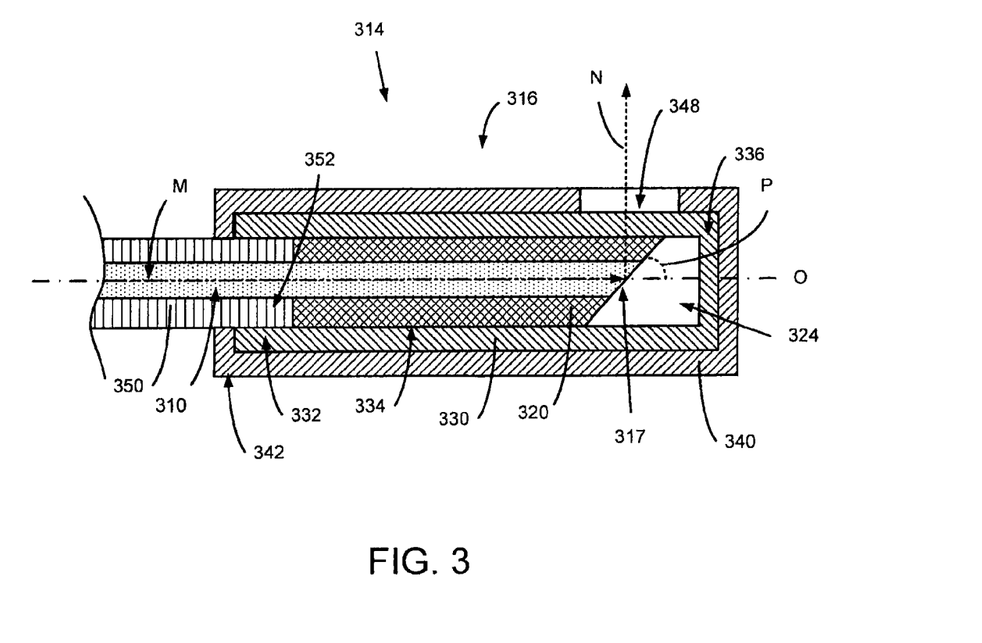
FIG. 3 is a side cross-sectional view of a side-fire assembly of a side-fire member that has a capillary component that defines a portion of an angled surface, according to an embodiment.

FIG. 3 is a side cross-sectional view of a side-fire assembly 316 of a side-fire member 314 that has a capillary component that defines a portion of an angled surface 317, according to an embodiment. The side-fire assembly 316 includes two capillary components—a first capillary component 320 and a second capillary component 330. As shown in FIG. 3, a distal end of the first capillary component 320 and a distal end of an optical fiber 310 collectively define the angled surface 317.

The first capillary component 320 is disposed outside of the optical fiber 310 of the side-fire member 314 and inside of the second capillary component 330. An outer cover 340 (e.g., a metallic cover, a plastic cover) may be coupled to and disposed outside of the second capillary component 330. The optical fiber 310, the first capillary component 320, and/or the second capillary component 330 can be made from a silica-based material (e.g., a pure silica material, a doped silica material). A jacket layer 350 is disposed around a portion of the optical fiber 310. Although not shown, the optical fiber 310 can have, for example, a fiber core, one or more cladding layers about the fiber core, and/or a buffer layer.

As shown in FIG. 3, laser energy M that is propagated along a longitudinal axis (or centerline) of the optical fiber 310 of the side-fire member 314 is redirected by an interface defined by the angled surface 317 and a gas (or a liquid) within a cavity 324. The cavity 324 is defined by the second capillary component 330 and the angled surface 317 so that the cavity 324 is a hermetically sealed volume. In this embodiment, the second capillary component 330 defines a cap 336 (e.g. a cap defining a wall around at least a portion of a hermetically sealed volume). The redirected laser energy N is transmitted through a portion of the first capillary component 320, a portion of the second capillary component 330, and an opening 348 defined by the outer cover 340.

As shown in FIG. 3, the angled surface 317 is defined by the optical fiber 310 and the first capillary component 320. The angled surface 317 can be a surface that is cleaved and/or polished after the first capillary component 320 has been heat-fused to the optical fiber 310. The angled surface 317 can have an angle P (with respect to a longitudinal axis O or centerline) of between approximately 5 degrees and 85 degrees. More details related to producing (e.g., manufacturing) the angled surface 317 are described below in connection with FIG. 5A through FIG. 6.

In some embodiments, the respective indices of refraction of components of the optical fiber 310 (e.g., one or more cladding layers of the optical fiber 310, a buffer layer of the optical fiber 310), the first capillary component 320, and the second capillary component 330, can be defined so that a desirable range of angles of incidence of the redirected laser energy N will be transmitted through the first capillary component 320 and the second capillary component 330 while other laser energy (e.g., stray laser energy) will be internally reflected (e.g., totally-internally reflected) without being transmitted through the first capillary component 320 and the second capillary component 330. More details related to angles of incidence, internal reflection within a capillary component and/or components of optical fibers are described in U.S. Provisional Application entitled, "Methods and Apparatus related to a Side-Firing Member having a Doped Silica Component," bearing Application No. 61/262,397, filed Nov. 18, 2009, which is incorporated herein by reference in its entirety.

The second capillary component 330 has a proximal end 332 that is disposed around a distal end 352 of the jacket layer 350. In some embodiments, the proximal end 332 of the second capillary component 330 can be coupled to the distal end 352 of the jacket layer 350. In some embodiments, the second capillary component 330 can be adhesively coupled to (e.g., adhesively coupled to using an epoxy), mechanically coupled to (e.g., mechanically coupled via a set screw and/or a press fit) the distal end 352 of the jacket layer 350. Portions of the second capillary component 330 that are distal to the proximal end 332 of the second capillary component 330 (such as portion 334) can be heat-fused to the first capillary component 320. Said differently, a portion of the second capillary component 330 can be coupled to the jacket layer 352 and a different portion of the second capillary component 330 can be heat-fused to the first capillary component 320.

In some embodiments, the second capillary component 330 can be coupled to the first capillary component 320 so that the cavity 324 will be a hermetically sealed volume without leakage of, for example, air between the first capillary component 320 and the second capillary component 330. In some embodiments, the second capillary component 330 can be coupled to the first capillary component 320 so that the first capillary component 320 and the second capillary component 330 collectively function (e.g., substantially function, function optically) as a single, monolithic capillary component. For example, in some embodiments, the first capillary component 320 can be heat-fused to the second capillary component 330 so that electromagnetic radiation will not be (e.g., substantially not be) reflected when the electromagnetic radiation passes between the first capillary component 320 and the second capillary component 330.

In this embodiment, the outer cover 340 has a proximal end 342 that is disposed around the proximal end 332 of the second capillary component 330. In some embodiments, the outer cover 340 can be made of a relatively malleable material that can be bent around (e.g., crimped around, plastically deformed around) the proximal end 332 of the second capillary component 330 (as shown in FIG. 3) after the outer cover 340 is disposed around the second capillary component 330. The outer cover 340 can be shaped so that the proximal end 332 of the outer cover 340 is coupled to the jacket layer 350. In some embodiments, the proximal end 332 of the outer cover 340 can be adhesively coupled to (e.g., adhesively coupled to using an epoxy), mechanically coupled to (e.g., mechanically coupled via a set screw and/or a press fit) the jacket layer 350. In some embodiments, the outer cover 340 can be shaped so that the proximal end 342 of the outer cover 340 is bent around the proximal end 332 of the second capillary component 330 without being coupled to (e.g., without touching) the jacket layer 350.

Figure 4:
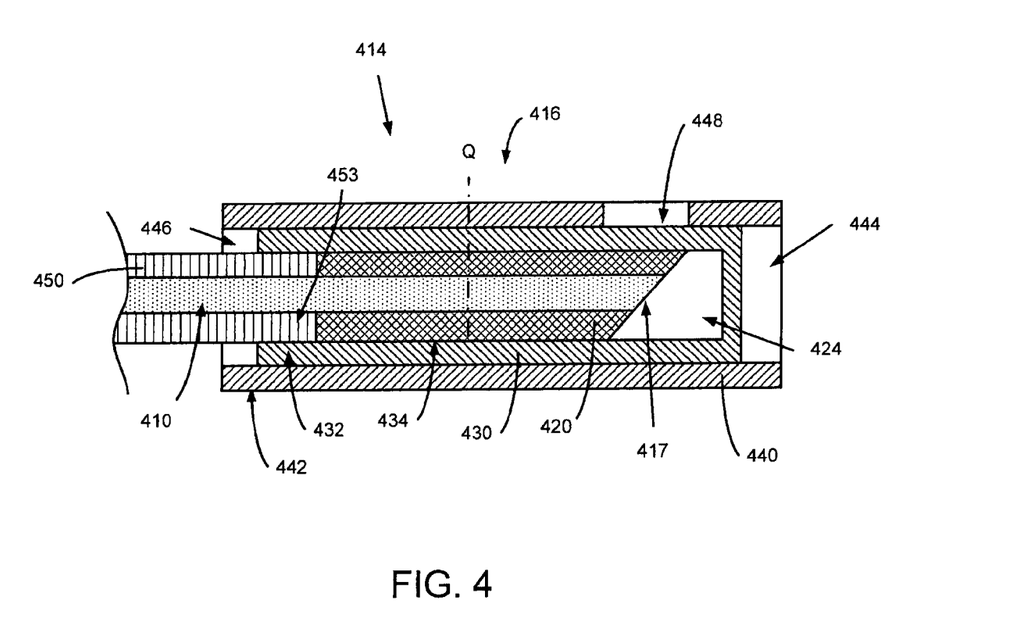
FIG. 4 is a side cross-sectional view of a side-fire assembly of a side-fire member that has tube-shaped outer cover, according to another embodiment.

FIG. 4 is a side cross-sectional view of a side-fire assembly 416 of a side-fire member 414 that has an outer cover 440 that defines a tube, according to another embodiment. The side-fire assembly 416 has a first capillary component 420 and a second capillary component 430. The first capillary component 420 is disposed outside of an optical fiber 410 of the side-fire member 414 and inside of the second capillary component 430. The outer cover 440 (e.g., a metallic cover) is coupled to and disposed outside of the second capillary component 430. The optical fiber 410, the first capillary component 420, and/or the second capillary component 430 can be made from a silica-based material (e.g., a pure silica material, a doped silica material). A jacket layer 450 is disposed around a portion of the optical fiber 410. Although not shown, the optical fiber 410 can have, for example, a fiber core, one or more cladding layers about the fiber core, and/or a buffer layer.

Although not shown in FIG. 4, laser energy propagated along a longitudinal axis (or centerline) of the optical fiber 410 of the side-fire member 414 can be redirected by an interface defined by an angled surface 417 and a gas (or a liquid) within a cavity 424. The cavity 424 can be defined by the second capillary component 430 and the angled surface 417. Although not shown in FIG. 4, redirected laser energy can be transmitted through a portion of the first capillary component 420, a portion of the second capillary component 430, and an opening 448 defined by the outer cover 440. As shown in FIG. 4, a distal end of the first capillary component 420 and a distal end of the optical fiber 410 collectively define the angled surface 417.

As shown in this embodiment, the outer cover 440 is a tube that defines a proximal end opening 446 and a distal end opening 444. The outer cover 440 defines a substantially straight lumen that can be slidably disposed around the second capillary component 430. The outer cover 440 can be coupled to (e.g., adhesively coupled to) the second capillary component 430. In some embodiments, the proximal end opening 446 and/or the distal end opening 444 can be filled with a material such as, for example, an adhesive material (e.g., an epoxy), a ceramic material, a metallic material, and/or a polymer-based material. The filling material can provide mechanical strength to the side-fire assembly 416 assembly. For example, an epoxy material in the proximal end opening 446 can bind the outer cover 440 to the jacket layer 450 and the second capillary component 430, and can substantially prevent the second capillary component 430 and the jacket layer 450 from being displaced in an undesirable fashion.

In this embodiment, the first capillary component 420 (e.g., an inner surface of the first capillary component 420) is heat-fused to the optical fiber 410 (e.g., an outer surface of the optical fiber 410) from the angled surface 417 to line Q. In some embodiments, the heat-fused portion can be longer than that shown in FIG. 4, or shorter than that shown in FIG. 4.

Figure 5A:
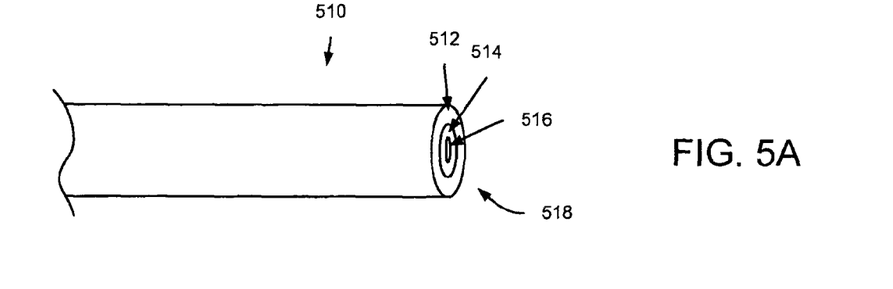
FIGS. 5A-5H are schematic diagrams that collectively illustrate a method for producing a side-fire assembly of a side-fire system, according to an embodiment.

FIG. 5A through FIG. 5H are schematic diagrams that collectively illustrate a method for producing a side-fire assembly of a side-fire system, according to an embodiment. FIG. 5A is a schematic diagram that illustrates an optical fiber 510 that has a jacket layer 512, a cladding layer 514, and a fiber core 516, according to an embodiment. As shown in FIG. 5A, the optical fiber 510 has a cleaved end 518.

Figure 5B:
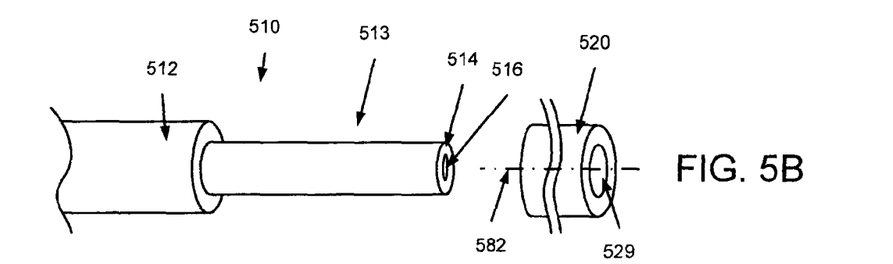

FIG. 5B is a schematic diagram that illustrates a stripped portion 513 of the optical fiber 510 (shown in FIG. 5A) and a first capillary component 520, according to an embodiment. A portion of the jacket layer 512 of the optical fiber 510 is removed (e.g., stripped away) to produce the stripped portion 513. In some embodiments, the stripped portion 513 can also be referred to as a remaining portion or as an exposed portion. The portion of the jacket layer 512 can be removed so that the first capillary component 520 can be moved over the cladding layer 514 and the fiber core 516.

Although not shown, in some embodiments, at least a portion (or all) of the cladding layer 514 and/or at least a portion of the fiber core 516 can also be removed to produce the stripped portion 513 of the optical fiber 510. Although not shown, in some embodiments, if the optical fiber 510 includes an additional and/or different layer (e.g., a buffer layer), at least a portion (or all) of the additional and/or different layer can be removed to produce the stripped portion 513.

The first capillary component 520 has a bore 529 (e.g., a lumen) along a longitudinal axis (or centerline) 582 of the first capillary component 520. The bore 529 of the first capillary component 520 is in fluid communication with an opening at each end (along the longitudinal axis 582) of the first capillary component 520. The first capillary component 520 can be cut from a length of a doped silica tubular (e.g., cylindrical) pre-form (not shown). The first capillary component 520 component can be cut from the pre-form using, for example, a laser energy cutting instrument and/or a mechanical cutting instrument. The pre-form can be cut along a plane that is substantially normal to a longitudinal axis or centerline of the pre-form. In some embodiments, the size of the bore 529 can be defined, in part, by removing a portion of a wall defining an existing bore within a pre-form using, for example, a reaming device.

In some embodiments, the first capillary component 520 can be uniformly or non-uniformly doped with, for example, fluorine and/or another suitable dopant. In some embodiments, the first capillary component 520 can be between a few millimeters (e.g., 50 mm) and several centimeters (e.g., 5 centimeters) long. In some embodiments, the first capillary component 520 can be cut from, for example, a doped silica tubular pre-form that has a doping concentration that is higher near an inner surface that defines the bore than at an outer surface of the pre-form, or vice versa.

Figure 5C:
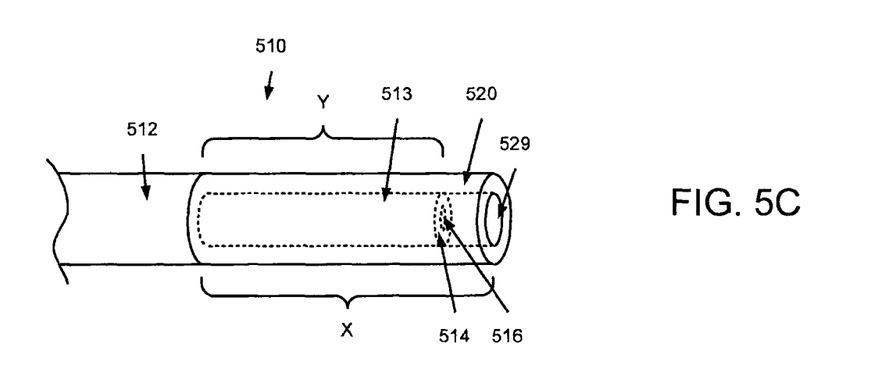

FIG. 5C is a schematic diagram that illustrates the first capillary component 520 disposed around the stripped portion 513 of the optical fiber 510 (shown in FIG. 5B), according to an embodiment. An inner diameter of the bore 529 of the first capillary component 520 can be defined so that it is, for example, at least a few micrometers larger than an outer diameter of the stripped portion 513 of the optical fiber 510 so that the first capillary component 520 can be moved (e.g., slidably moved) over the stripped portion 513 in a desirable fashion.

In this embodiment, a length X of the first capillary component 520 is longer than a length Y of the stripped portion 513 of the cladding layer 514. In some embodiments, the length X of the first capillary component 520 can be equal to or shorter than the length Y of the stripped portion 513 of the cladding layer 514.

In this embodiment, a proximal end of the first capillary component 520 is moved over the stripped portion 513 until the proximal end of the first capillary component 520 is in contact with a distal end of the jacket layer 512. In some embodiments, the proximal end of the first capillary component 520 can be moved over the stripped portion 513 so that the proximal end of the first capillary component 520 is not in contact with the distal end of the jacket layer 512.

Figure 5D:
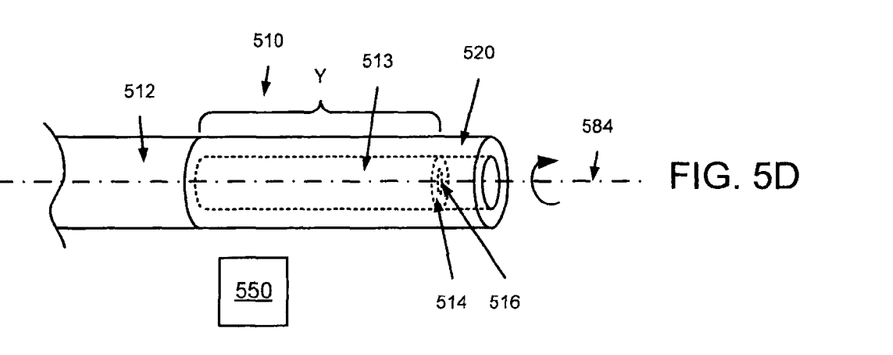

After the first capillary component 520 has been disposed over the stripped portion 513 of the optical fiber 510, the first capillary component 520 can be heat-fused to the optical fiber 510. FIG. 5D is a schematic diagram that illustrates the first capillary component 520 being heat-fused (during a first heat-fusing process) to the stripped portion 513 of the optical fiber 510 using a heat source 550, according to an embodiment. In some embodiments, the first capillary component 520 and optical fiber 510 can be heated using, for example, the heating source 550 (e.g., a torch, a flame, an electrical heating element, a laser source) until the first capillary component 520 and optical fiber 510 are fused. The first capillary component 520 and optical fiber 510 can be rotated about a longitudinal axis 584 of the optical fiber 510 while being heated.

In some embodiments, the first capillary component 520 can be heat-fused to the entire length Y of the stripped portion 513 of the optical fiber 510 of the side-fire assembly. In some embodiments, the first capillary component 520 can be heat-fused to only a portion (or portions) of the length Y of the stripped portion 513 of the optical fiber 510.

Figure 5E:
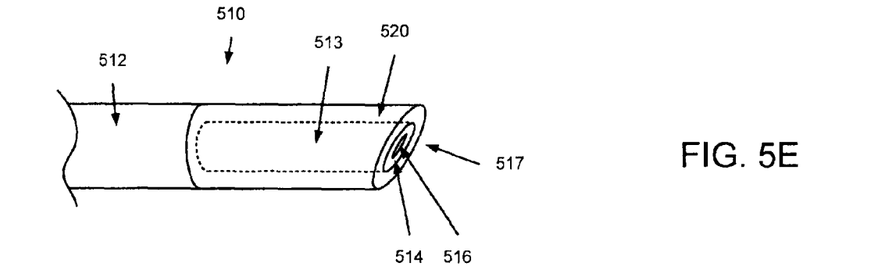

FIG. 5E is a schematic diagram that illustrates an angled surface 517 defined by at least a portion of the first capillary component 520 and the stripped portion 513 of the optical fiber 510, according to an embodiment. The angled surface 517 of the side-fire assembly is defined after the first capillary component 520 has been heat-fused to the stripped portion 513. The angled surface 517 can be initially cut using, for example, a laser energy cutting instrument and/or a mechanical cutting instrument. After the angled surface 517 has been initially cut, the angled surface 517 can be polished using, for example, a mechanical polishing instrument.

The angled surface 517 is defined by the first capillary component 520 and the stripped portion 513 of the optical fiber 510 so that the angled surface 517 has a larger surface area than if the angled surface 517 were defined using only the stripped portion 513 of the optical fiber 510. The angled surface 517 is defined after the first capillary component 520 has been heat-fused to the stripped portion 513, so that a portion of the angled surface 517 defined by the stripped portion 513 of the optical fiber 510 can be defined in a desirable fashion (e.g., defined as a substantially flat surface without warps, precisely defined). In contrast, if the portion of the angled surface 517 defined by the stripped portion 513 of the optical] fiber 510 were instead produced before the first capillary component 520 were heat-fused to the optical fiber 510, the heat-fusing process could cause the portion of the angled surface 517 to be deformed in an undesirable fashion. In some embodiments, the portion of the angled surface 517 defined by the stripped portion 513 of the optical fiber 510 can be referred to as the critical portion of the angled surface.

Figure 5F:
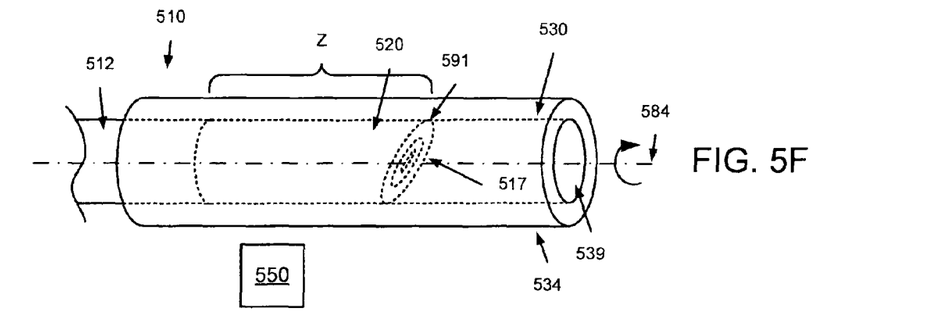

FIG. 5F is a schematic diagram that illustrates a second capillary component 530 disposed over the angled surface 517, according to an embodiment. The second capillary component 530 can have a bore 539 moved (e.g., slidably moved) over the angled surface 517 after the angled surface 517 has been defined. After the second capillary component 530 is disposed over the angled surface 517, the second capillary component 530 can be heat-fused to the first capillary component 520. In some embodiments, the second capillary component 530 and first capillary component 520 can be heated using, for example, the heating source 550 (or a different heating source (not shown)) until the second capillary component 530 and first capillary component 520 are fused (during a second heat-fusing process). In some embodiments, the second capillary component 530 and first capillary component 520 (as well as the optical fiber 510) can be rotated about a longitudinal axis 584 of the optical fiber 510 while being heated by heat source 550.

In some embodiments, the second capillary component 530 can be heat-fused to the entire length Z of the first capillary component 520 of the side-fire assembly. In some embodiments, the second capillary component 530 can be heat-fused to only a portion (or portions) of the length Z of the first capillary component 520. Although not shown, in some embodiments, the heating associated with FIG. 5D and the heating associated with FIG. 5F can be performed using different heating sources. Although not shown, in some embodiments, the second capillary component 530 can be, for example, adhesively coupled to the first capillary component 520 rather than being heat-fused to the first capillary component 520.

In some embodiments, the second capillary component 530 can be uniformly or non-uniformly doped with, for example, fluorine and/or another suitable dopant. In some embodiments, the second capillary component 530 can be between a few millimeters (e.g., 50 mm) to several centimeters (e.g., 5 centimeters) long. In some embodiments, the second capillary component 530 can be cut from, for example, a doped silica tubular pre-form that has a doping concentration that is higher near an inner surface that defines the bore than at an outer surface of the pre-form, or vice versa. In some embodiments, the second capillary component 530 can be made from substantially pure silica (substantially without a dopant).

Although the heat-fusing process can cause, for example, deformation (e.g., plastic deformation) of portions of the angled surface 517 near, for example, an edge 591 of the angled surface 517, the edge 591 of the angled surface 517 may not impact performance of the side-firing functionality of the optical fiber 510 in an undesirable fashion. In some embodiments, the edge 591 of the angled surface 517 may not be needed to redirect laser energy (or may not impact redirection of laser energy) propagated along the optical fiber 510 of the side-fire assembly. Moreover, the critical portion of the angled surface 517 may not be undesirably impacted (e.g., undesirably warped) by the heat-fusing of the second capillary component 530 to the first capillary component 520.

In some embodiments, the first capillary component 520 can function as a thermal insulator that protects the critical portion of the angled surface 517 defined by the optical fiber 510 during heat-fusing of the second capillary component 530 to the first capillary component 520. In some embodiments, a thickness of the first capillary component 520 can be defined so that the first capillary component 520 can function as a thermal insulator in a desirable fashion during heat-fusing of the second capillary component 530 to the first capillary component 520. In other words, at least a portion of the first capillary component 520 can substantially insulate the optical fiber 510 from the heat present at (and around) the interface of the first capillary component 520 and the second capillary component 530 during heat fusing of the second capillary component 530. In some embodiments, for example, the thickness of the first capillary component 520 can be defined based on, for example, a heat transfer coefficient of the first capillary component 520, a heat transfer coefficient of the second capillary component 530, and/or a melting point of the critical portion of the angled surface 517.

In some embodiments, the first capillary component 520 can be heat-fused (during a first heat-fusing process) to the second capillary component 530 to a lesser extent (e.g., for a shorter duration, at a lower temperature, over a smaller area) than the first capillary component 520 is heat-fused (during a second heat-fusing process) to the optical fiber 510. For example, the first capillary component 520 can be heat-fused to the optical fiber 510 during a first heat-fusing process so that an entire length of an inner surface of the first capillary component 520 is heat-fused to an outer surface of the optical fiber 510. After the angled surface 517 is defined from the first capillary component 520 and the optical fiber 510, only a portion of the second capillary component 530 can be heat-fused during a second heat-fusing process to the first capillary component 520 so that the angled surface 517 will not be impacted by the second heat-fusing process in an undesirable fashion.

Figure 5G:
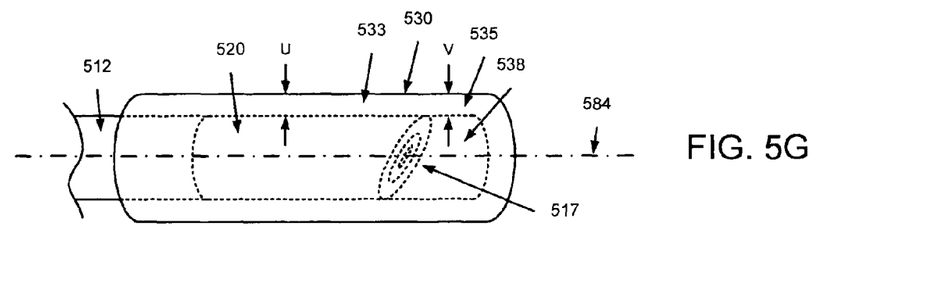

Although not shown in FIG. 5F, in some embodiments, a distal end 534 of the second capillary component 530 can be heated while being pulled in distal direction (away from the angled surface 517) until an enclosure is formed. In other words, a force in the distal direction (away from the angled surface 517) can be applied on the distal end 534 of the second capillary component 530 while it is being heated. The second capillary component 530 can be heated until the second capillary component 530 softens and can be pulled. As the distal end 534 of the second capillary component 530 is heated and pulled, the second capillary component 530 can plastically deform until at least a portion of the distal end 534 of the second capillary component 530 is separated from a proximal portion of the second capillary component 530 to define the shape of the second capillary component 530 shown in FIG. 5G. FIG. 5G is a schematic diagram that illustrates an enclosure 538 (e.g., a hermetically sealed enclosure) defined by the second capillary component 530, according to an embodiment. More details related to a heating and pulling process are described in U.S. Provisional Application entitled, "Methods and apparatus related to a Side-Firing Member having a Doped Silica Component," bearing Application No. 61/262, 397, filed Nov. 18, 2009, which has been incorporated herein by reference in its entirety.

Referring back to FIG. 5F, in some embodiments, the heating and/or pulling discussed in connection with FIG. 5F may not be performed coincidentally. For example, a portion of the distal end of the second capillary component 530 can be heated before the distal end of the second capillary component 530 is pulled. In some embodiments, the optical fiber 510 and the second capillary component 530 can be rotated, for example, around the longitudinal axis 584 while being heated and/or pulled. In some embodiments, the heating associated with the formation of the enclosure 538 shown in FIG. 5G can be performed using heat source 550, or a different heat source (not shown). In some embodiments, the heating associated with the fusing of the first capillary component 520 to the second capillary component 530 and the heating associated with the formation of the enclosure 538 shown in FIG. 5G can be performed within the same heating cycle, or can be performed separately (e.g., at a different time and space).

Referring back to FIG. 5G, in some embodiments, the enclosure 538 of the side-fire assembly can be filled with, for example, a gas such as air. In some embodiments, the second capillary component 530 can have a portion 533 that is heat-fused to the first capillary component 520 and a portion 535 that defines at least a portion of the enclosure 538 (and is not heat-fused to the first capillary component 520). A thickness V of the portion 535 can be different than a thickness U of the portion 533. For example, in some embodiments, the thickness V of the portion 535 can be defined when being heated and pulled as described in connection with FIG. 5F, so that the thickness V is greater than the thickness U. Accordingly, the portion 535 can have a greater mechanical strength than if the portion 535 had a thickness less than or equal to thickness U.

Figure 5H:
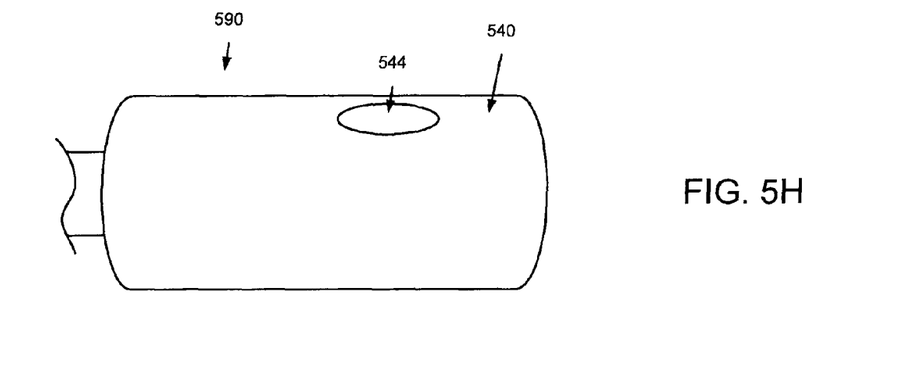

FIG. 5H is a schematic diagram that illustrates an outer cover 540 of the side-fire assembly, according to an embodiment. The outer cover 540 can be coupled to the second capillary component 530 (not shown in FIG. 5H). In some embodiments, the outer cover 540 can configured to be moved (e.g., slidably moved) over the second capillary component 530. As shown in FIG. 5H, the outer cover 540 can have an opening 544 configured to permit transmission of at least a portion of laser energy redirected by the angled surface 517 (not shown in FIG. 5H).

Figure 6:
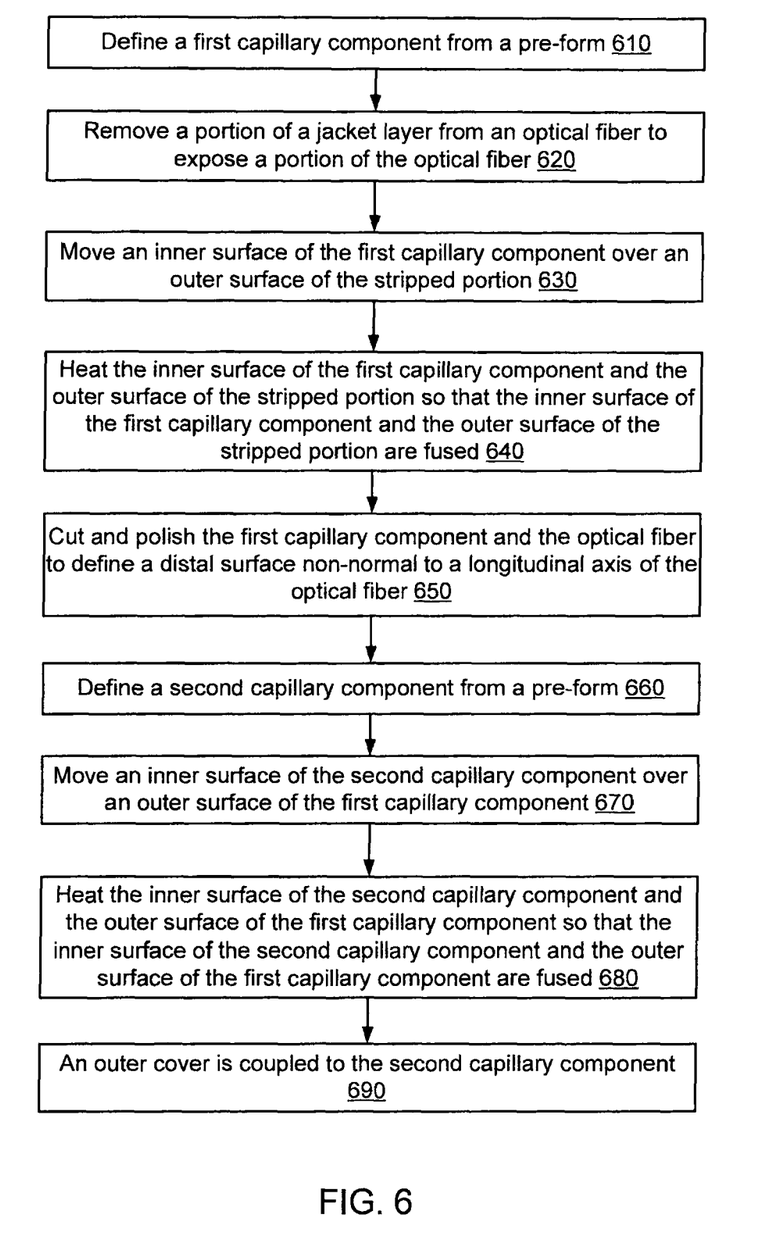
FIG. 6 is a flowchart that illustrates a method for producing a side-fire assembly of a side-fire system, according to an embodiment.

FIG. 6 is a flowchart that illustrates a method for producing a side-fire assembly of a side-fire system, according to an embodiment. As shown in FIG. 6, a first capillary component is defined from a pre-form, at 610. Specifically, the first capillary component can be cut from a pre-form that is doped or undoped. The first capillary component can be machined further after being cut from the pre-form. For example, a bore of the first capillary component can be reamed after the first capillary component has been cut from the pre-form.

A portion of a jacket layer from an optical fiber is removed to expose a portion of the optical fiber, at 620. In some embodiments, the jacket layer can be a polymer-based jacket layer. In some embodiments, the portion of the jacket layer can be removed using a stripping tool.

An inner surface of the first capillary component is moved over an outer surface of the stripped portion, at 630. The inner surface of the first capillary component can define a bore. In some embodiments, the inner surface of the first capillary component can define a shape that can substantially correspond with a shape of the outer surface of the stripped portion. For example, the inner surface of the first capillary component can define a tapered shape that substantially corresponds with a tapered shape of the outer surface of the stripped portion. The outer surface of the stripped portion can be tapered downward from a proximal end of the stripped portion to a distal end of the stripped portion.

The inner surface of the first capillary component and the outer surface of the stripped portion are heated (during a first heat-fusing process) so that the inner surface of the first capillary component and the outer surface of the stripped portion are fused, at 640. In some embodiments, only portions of the outer surface of the stripped portion can be heat-fused to the inner surface of the first capillary component. Similarly, in some embodiments, only portions of the inner surface of the first capillary component can be heat-fused to the outer surface of the stripped portion. In some embodiments, conditions (e.g., a temperature, a duration, a directionality) of the heating can be defined so that the inner surface of the first capillary component and the outer surface of the stripped portion define an abrupt interface or define an imprecise interface (e.g., substantially mixed to define an imprecise (blurred) interface).

The first capillary component and the optical fiber are cut and polished to define a distal surface non-normal (and non-parallel) to a longitudinal axis of the optical fiber, at 650. Specifically, the first capillary component and the optical fiber can be cut and polished to define an angled surface configured to redirect laser energy propagating along the optical fiber and incident on an interface defined at least in part by the angled surface. In some embodiments, the cut and/or the polishing can be performed using a mechanical instrument.

A second capillary component can be defined from a preform, at 660. In some embodiments, the first capillary component can be cut from a pre-form that is doped or undoped. The second capillary component can be machined further after being cut from the pre-form. For example, a bore of the second capillary component can be reamed after the second capillary component has been cut from the pre-form.

An inner surface of the second capillary component is moved over an outer surface of the first capillary component, at 670. The inner surface of the second capillary component can define a bore. In some embodiments, the inner surface of the second capillary component can define a shape that can substantially correspond with a shape of the outer surface of the first capillary component. For example, the inner surface of the second capillary component can define a tapered shape that substantially corresponds with a tapered shape of the outer surface of the first capillary component.

The inner surface of the second capillary component and the outer surface of the first capillary component can be heated (during a first heat-fusing process) so that the inner surface of the second capillary component and the outer surface of the first capillary component are fused, at 680. In some embodiments, only portions of the outer surface of the first capillary component can be heat-fused to the inner surface of the second capillary component. Similarly, in some embodiments, only portions of the inner surface of the second capillary component can be heat-fused to the outer surface of the first capillary component. In some embodiments, conditions (e.g., temperature, duration, directionality) of the heating can be defined so that the inner surface of the second capillary component and the outer surface of the first capillary component define an abrupt interface or define an imprecise interface (e.g., substantially mixed to define an imprecise (blurred) interface).

An outer cover is coupled to the second capillary component, at 690. In some embodiments, the outer cover can be a metal cover. In some embodiments, the outer cover can have an opening through which laser energy redirected from the distal surface can pass. In some embodiments, the outer cover can be coupled to the second capillary component using an adhesive. In some embodiments, the outer cover can define a cap or can be a tube. If the outer cover is a tube, adhesive can be used to fill a distal opening defined by the tube and/or a proximal opening defined by the tube after the tube is disposed around the second capillary component.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described. For example, heat-fusing of a capillary component to an optical fiber can be performed simultaneously using multiple heat sources.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. An apparatus, comprising:
a first capillary extending along a longitudinal axis and having an open distal end, wherein a flat distal end face of the open distal end of the first capillary is perpendicular to the longitudinal axis; a second capillary disposed outside of the first capillary and having an inner surface and a flat open distal end face, wherein a portion of the inner surface of the second capillary is heat-fused to an outer surface of the first capillary;
an outer cover cap coupled to and disposed outside of the second capillary, and forming a distal end of the apparatus and an internal flat surface; and
an optical fiber, a portion of the optical fiber disposed inside of the first capillary and having an outer surface, wherein a portion of the outer surface of the optical fiber is heat-fused to an inner surface of the first capillary, the optical fiber having an angled distal surface configured to reflect electromagnetic radiation propagated along a longitudinal axis of a distal end portion of the optical fiber in a lateral direction through the inner surface of the first capillary and the inner surface of the second capillary, and the outer cover cap is configured to reflect stray laser energy internal to the apparatus, wherein the distal end face of the first capillary and the distal end face of the second capillary extend distally beyond the distal end surface of the optical fiber and the internal flat surface of the outer cover cap abuts the distal end face of the first capillary and the distal end face of the second capillary.

2. The apparatus of claim 1, wherein the optical fiber has a dopant different than a dopant of the first capillary component, and wherein the portion of the optical fiber includes at least one cladding layer.

3. The apparatus of claim 1, wherein the distal surface of the optical fiber and the outer cover define at least a portion of an enclosure.

4. The apparatus of claim 1, wherein the electromagnetic radiation is emitted from a Ho:YAG laser source, Nd:YAG laser source, a semiconductor laser diode, or a laser source having a non-linear crystal element.

5. The apparatus of claim 1, wherein the fiber is a low hydroxyl fiber.

6. The apparatus of claim 1, wherein the first capillary and the second capillary are made of silica-based material and the outer cover cap is metallic or made of polymer-based material.

7. An apparatus, comprising: a side-fire laser fiber including a first capillary extending along a longitudinal axis and having an open distal end and an optical fiber, the open distal end of the first capillary having a flat distal end face perpendicular to the longitudinal axis, the first capillary being heat-fused to an outer surface of the optical fiber, the optical fiber having an angled distal end surface being within a plane non-normal to a longitudinal centerline of the optical fiber and configured to reflect laser radiation propagated along a longitudinal axis of a distal end portion of the optical fiber in a lateral direction through the first capillary and the second capillary;
a second capillary being heat-fused to an outer surface of the first capillary and having an open flat distal end face, the distal end face of the first capillary and the distal end face of the second capillary each extending distally beyond the distal end surface of the laser fiber; and
an outer cover cap coupled to and disposed outside the second capillary, the outer cover having a side opening and a portion distal of the side opening that surrounds the second capillary, wherein the outer cover cap includes an internal planar surface abutting the distal end face of the first capillary and the distal end face of the second capillary.

8. The apparatus of claim 7, wherein at least one of an entirety of the outer surface of the first capillary component is heat-fused to the second capillary component or an entirety of the inner surface of the first capillary component is heat-fused to the outer surface of the optical fiber.

9. The apparatus of claim 7, wherein the outer surface of the first capillary component is heat-fused to the second capillary component at a first region, and the outer surface of the first capillary component is heat-fused to the second capillary component at a second region noncontiguous with the first region.

10. The apparatus of claim 7, wherein the first capillary component has a dopant profile different than a dopant profile of the second capillary component.

11. The apparatus of claim 7, wherein the first capillary component has an index of refraction that is different than an index of refraction of the optical fiber, and the index of refraction of the first capillary component is substantially equal to an index of refraction of the second capillary component.

12. The apparatus of claim 7, wherein the laser radiation is emitted from a Ho:YAG source, Nd:YAG source, a semiconductor laser diode, or a laser source having a non-linear crystal element.

13. The apparatus of claim 7, wherein the fiber is a low hydroxyl fiber.

14. The apparatus of claim 7, wherein the first capillary and the second capillary are made of silica-based material and the outer cover cap is metallic or made of polymer-based material.

15. An apparatus, comprising: a first capillary extending along a longitudinal axis and having an inner surface and an open distal end, the open distal end of the first capillary having a flat distal end face perpendicular to the longitudinal axis;

an optical fiber disposed inside of the first capillary, the inner surface of the first capillary being heat-fused with an outer surface of the optical fiber, the optical fiber having an angled distal end surface configured to reflect electromagnetic radiation propagated along a longitudinal axis of a distal end portion of the optical fiber in a lateral direction through the inner surface of the first capillary;

a second capillary disposed outside of the first capillary component, the second capillary having a tubular construction open at a proximal and distal end, the distal end of the second capillary having an open flat distal end face, wherein the distal end face of the first capillary and the distal end face of the second capillary extend distally beyond the distal end surface of the optical fiber; and an outer cover cap coupled to and disposed outside the second capillary, wherein the outer cover cap includes an internal planar surface abutting the distal end face of the first capillary and the distal end face of the second capillary.

16. The apparatus of claim 15, wherein the distal end faces of the first and second capillary components include coterminous flat ends.

17. The apparatus of claim 16, wherein the outer cover includes a planar inner surface abutting the coterminous flat ends of the first and second capillary components.

18. The apparatus of claim 12, wherein the electromagnetic radiation is emitted from a Ho:YAG source, Nd:YAG source, a semiconductor laser diode, or a laser source having a non-linear crystal element.

19. The apparatus of claim 15, wherein the fiber is a low hydroxyl fiber.

20. The apparatus of claim 15, wherein the first capillary and the second capillary are made of silica-based material and the outer cover cap is metallic or made of polymer-based material.

* * * * *